United States Patent [19]
West

[11] Patent Number: 5,589,483
[45] Date of Patent: Dec. 31, 1996

[54] ISOQUINOLINE POLY (ADP-RIBOSE) POLYMERASE INHIBITORS TO TREAT SKIN DISEASES ASSOCIATED WITH CELLULAR SENESCENCE

[75] Inventor: Michael D. West, Belmont, Calif.

[73] Assignee: Geron Corporation, Menlo Park, Calif.

[21] Appl. No.: 361,798

[22] Filed: Dec. 21, 1994

[51] Int. Cl.$^6$ .................................................. A61K 31/47
[52] U.S. Cl. .............................................. 514/310; 514/309
[58] Field of Search ................................. 514/309, 312, 514/310

[56] References Cited

U.S. PATENT DOCUMENTS 5,032,617  7/1991  Lee et al. .
5,041,653  8/1991  Lee et al. .
5,215,738  6/1993  Lee et al. .
5,272,057  12/1993  Smulson et al. .

FOREIGN PATENT DOCUMENTS 9118591  12/1991  WIPO .

*Primary Examiner*—Theodore J. Criares
*Attorney, Agent, or Firm*—John R. Storella; William M. Smith; Kevin R. Kaster

[57]  ABSTRACT

Inhibition of the enzyme poly (ADP-ribose) polymerase can delay the onset of senescence and inhibitors of the enzyme can be used to treat diseases caused or exacerbated by cellular senescence.

3 Claims, 2 Drawing Sheets

ISOQUINOLINE POLY (ADP-RIBOSE) POLYMERASE INHIBITORS TO TREAT SKIN DISEASES ASSOCIATED WITH CELLULAR SENESCENCE

BACKGROUND OF THE INVENTION

1. Field of the Invention

The present invention relates to the fields of molecular biology, gerontology, and medical pharmacology and diagnostics.

2. Description of Related Art

There is substantial evidence that somatic cells have a finite replicative capacity (Hayflick and Moorhead, 1961, *Exp. Cell Res.* 25: 585–621; Hayflick, 1965, *Exp. Cell Res.* 37: 614–636; and Hayflick, 1970, *Exp. Geront.* 5: 291–303) and that this process is a major etiological factor in aging and age-related disease (Goldstein, 1990, *Science* 249: 1129–1133; Stanulis-Praeger, 1987, *Mech. Ageing Dev.* 38: 1–48; and Walton, 1982, *Mech. Ageing Dev.* 19: 217–244). As cells undergo replicative senescence in vitro and in vivo, the cells not only lose the ability to divide in response to growth stimuli, but there are also significant deleterious changes in the pattern of gene expression (West, 1994, *Arch. Derm.* 130: 87–95). As an individual grows older, senescent cells make up an increasing percentage of the cells present in the tissues of the aging individual. The altered pattern of gene expression exhibited by senescent cells is likely to contribute significantly to age-related pathologies. Reversal of, or a delay in the onset of, senescence should provide an effective therapy for diseases in which replicative senescence plays a role.

There is growing evidence that the fundamental cause of cellular senescence is the progressive loss or telomeric repeated DNA in somatic cells that lack the enzyme designated telomerase (see Harley, 1991, *Telomere loss: Mitotic clock or genetic time bomb? Mut. Res.* 256:271–282). There is currently no consensus as to the molecular mechanisms that recognize the shortened telomeres in aged cells and cause a cell cycle arrest at the $G_1/S$ interface, but this arrest may be caused by a DNA checkpoint arrest in which the senescent cell recognizes the shortened telomere as damaged DNA and causes cell cycle arrest similar to that observed in normal cells, which arrest their growth in the presence of DNA damage.

The mammalian enzyme Poly (ADP-Ribose) Polymerase (PADPRP) has been implicated in the signalling of DNA damage. PADPRP activity is higher in isolated nuclei of SV40-transformed fibroblasts than in those of untransformed fibroblasts; leukemic cells show higher enzyme activity than normal leukocytes; and colon cancers show higher enzyme activity than normal colon mucosa (see Miwa et al., 1977, *Arch. Biochem. Biophys.* 181: 313–321; Burzio et al., 1975, *Proc. Soc. Exp. Biol. Med.* 149:933–938; and Hirai et al., 1983, *Cancer Res.* 43:3441–3446. These observations led to the conclusion that the enzyme activity responds to DNA damage and parallels DNA repair. Supporting this conclusion is the observation that the reduction of the activity of the enzyme by certain drugs increases DNA amplification and consequent oncogenesis in cells (see Harris, 1985, *Int. J. Radiat. Biol.* 48: 675–690).

More recent work has focused on the mechanism by which PADPRP modulates DNA replication and repair (see Smulson and Sugimura, eds., "Novel ADP-ribosylations of regulatory enzymes and proteins," Elsevier, N.Y. (1980)). Such studies have identified PADPRP as an ~113 kDa protein that uses NAD as a substrate in the formation of poly (ADP-ribose) chains at sites on many nuclear proteins. The enzyme binds tightly to DNA and requires DNA strand breaks for activity (see Benjamin and Gill, 1980, *J. Biol. Chem.* 255: 10502–10508). The PADPRP enzyme system appears to function in response to transient and localized DNA strand breaks in cells that may arise through a variety of processes including DNA repair, replication, recombination, and gene rearrangement (see Alkhatib et al., 1987, *Proc. Natl. Acad. Sci. USA* 84:1224–1228). The cDNA corresponding to the PADPRP gene has also been cloned and sequenced (see Cherney et al., 1987, *Proc. Natl. Acad. Sci. USA* 84:8370), and methods for detecting a predisposition to cancer arising out of mutations in the PADPRP gene have been reported (see U.S. Pat. No. 5,272,057).

Inhibitors of PADPRP have also been developed, primarily for the purpose of enzymatic studies (see Banasik et al., 1992, *J. Biol. Chem.* 267: 1569–1575) and for use in cancer and anti-viral therapies (see PCT patent publication No. 91/18591). PADPRP inhibitors have been reported to be effective in radiosensitizing hypoxic tumor cells (see U.S. Pat. Nos. 5,032,617; 5,215,738; and 5,041,653). These compounds can also be used to prevent tumor cells from recovering from potentially lethal damage of DNA after radiation therapy, presumably by their ability to prevent DNA repair.

One weak inhibitor of PADPRP known as kinetin (Althaus, F. R., and Richter, C., 1987, *ADP-ribosylation of Proteins* (Springer-Verlag); see p. 26) has also been reported to delay the onset of aging characteristics in human fibroblasts (see Rattan and Clark, 1994, *Biochem. Biophys. Res. Comm.* 201(2): 665–672). However, the researchers speculated that kinetin acted through receptor-mediated action on the components of protein synthetic machinery, improving the efficiency of various maintenance and repair pathways such as fidelity of protein synthesis, scavenging free radicals, and removing abnormal and damaged macromolecules. Moreover, the researchers stated that the anti-aging effects of kinetin were not accompanied by an increase in cell culture lifespan in terms of maximum proliferative capacity in vitro.

Consequently, there remains a need for compounds that can delay the onset of senescence and extend the maximum proliferative capacity of cells in vivo and in vitro. The present invention meets this and other needs.

SUMMARY OF THE INVENTION

In a first aspect, the present invention provides a method to extend the lifespan and proliferative capacity of cells, which method comprises administering a therapeutically effective amount of a PADPRP inhibitor to said cells under conditions such that PADPRP activity is inhibited. The method is especially useful in treating disease or disease conditions induced or exacerbated by cellular senescence. In particular, the method of the invention is useful in treating skin aging, Alzheimer's disease, atherosclerosis, osteoarthritis, osteoporosis, age-related macular degeneration, muscular dystrophy, and immune senescence, including diseases, such as AIDS, that result in immune senescence.

In a second aspect, the present invention provides compounds and formulations useful in the method. Preferred compounds for use in the present method include 3-hydroxybenzamide, 3-acetamidobenzamide, 3-methoxybenzamide, 3-methylbenzamide, 3-fluorobenzamide, 2-methoxybenzamide, 3-chlorobenzamide, benzamide, 4-amino-1,8-naphthalimide, 2H-benz[c]isoquinolin-1-one [6(5H)

-phenanthridinone], 2-nitro-6(5H)-phenanthridinone, 1,5-dihydroxyisoquinoline, 2H-benz[de]isoquinoline-1,3-dione, (1,8-naphthalimide), 2-methyl-4(3H)-quinazolinone, 1-hydroxyisoquinoline (isocarbostyril), 2,4(1H,3H)-quinazolinedione (benzoyleneurea), chlorthenoxazin, 4-hydroxyquinazoline, 1(2H)-phthalaz inone, 2-phenylchromone (flavone), 3-aminophthalhydrazide (luminol), N-formyl luminol, arachidonic acid, oleic acid, linoleic acid, and nicotinamide.

These and other aspects of the invention are described in more detail below, beginning with a brief description of the accompanying drawings.

DESCRIPTION OF THE PREFERRED EMBODIMENTS

Figure 1:
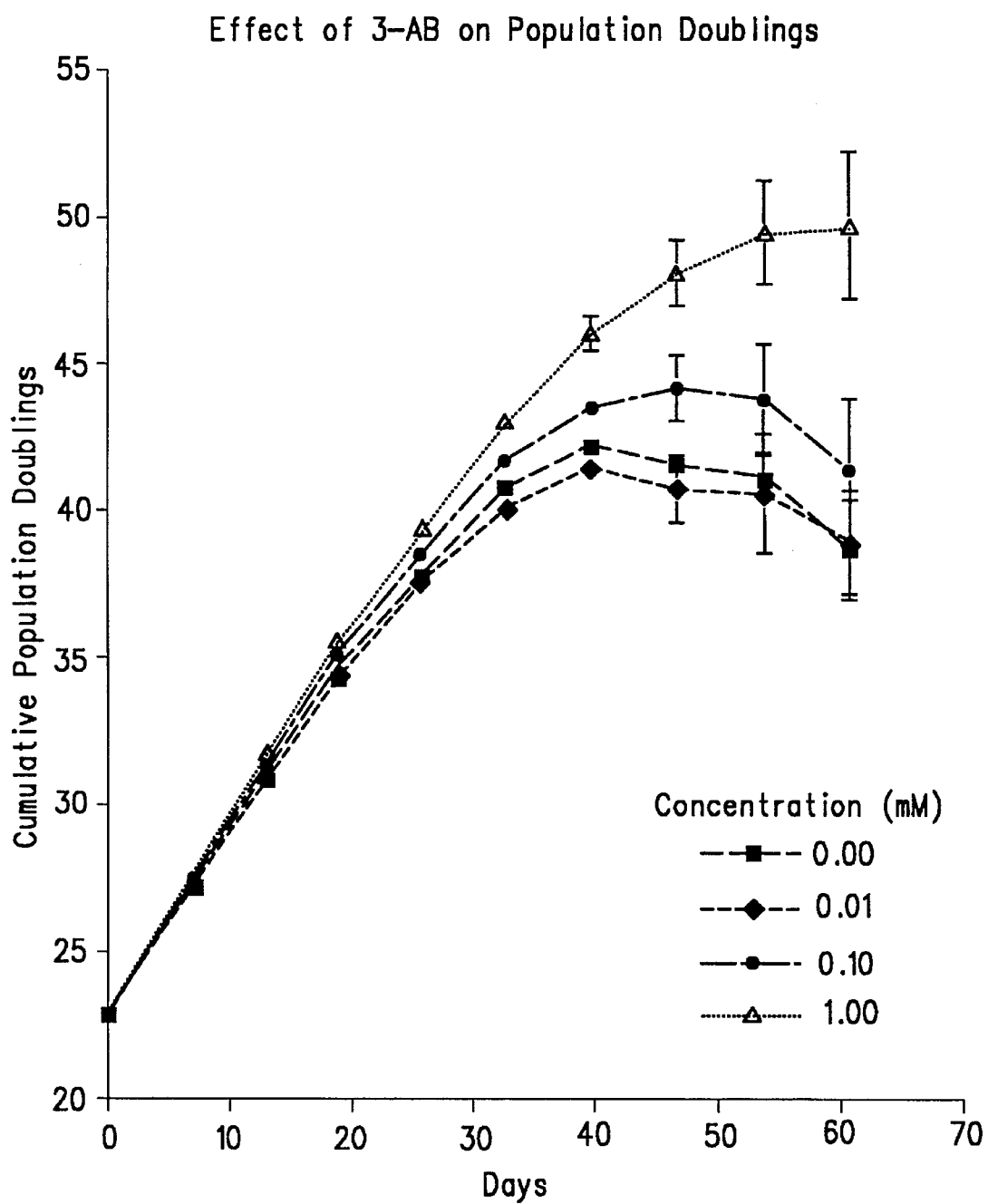
FIG. 1 shows the results of treating human fibroblast cells (W138 cells) in vitro with varying concentrations of 3-aminobenzamide (3-AB) as measured in the maximum achievable cumulative population doublings. The X-axis shows the number of days in culture, while the Y-axis shows the cumulative population doublings observed for each of the treated cell cultures. A significant increase in the maximum achievable cumulative population doublings was observed with cells treated with 1 mM 3-AB.

The present invention provides a method to extend the lifespan and proliferative capacity of cells, which method comprises administering a therapeutically effective amount of a PADPRP inhibitor to said cells under conditions such that PADPRP activity is inhibited. The method is especially usefulin treating disease or disease conditions induced or exacerbated by cellular senescence. In particular, the method of the invention is useful in treating skin aging, Alzheimer's disease, atherosclerosis, osteoarthritis, osteoporosis, muscular dystrophy, age-related macular degeneration, and immune senescence, including diseases, such as AIDS, that result in immune senescence.

Compounds for use in the present method include any compound that specifically inhibits PADPRP, such as those disclosed in Banasik et al., 1992, J. Biol. Chem. 267: 569–1575, and U.S. Pat. Nos. 5,032,617; 5,215,738; and 5,041,653. Preferred compounds of the invention are shown in Table 1, below.

TABLE 1

| PADPRP Inhibitors | |
|---|---|
| Compound | IC$_{50}$ (μM) |
| Benzamide analogues: | |
| 3-Hydroxybenzamide | 9.1 |
| 3-Acetamidobenzamide | 12 |
| 3-Methoxybenzamide | 17 |
| 3-Methylbenzamide | 19 |
| 3-Fluorobenzamide | 20 |
| 2-Methoxybenzamide | 20 |
| 3-Chlorobenzamide | 22 |

TABLE 1-continued

| PADPRP Inhibitors | |
|---|---|
| Compound | IC$_{50}$ (μM) |
| Benzamide | 22 |
| 3-Aminobenzamide | 33 |
| 5-Acetamidosalicylamide | 45 |
| m-Phthalamide (isophthalamide) | 50 |
| 3-Bromobenzamide | 55 |
| 2-Hydroxybenzamide (salicylamide) | 82 |
| Fatty Acids: | |
| Arachidonic acid | 44 |
| Linoleic acid | 48 |
| Oleic acid | 82 |
| Other Compounds: | |
| 4-amino-1,8-naphthalimide | 0.18 |
| 2H-Benz[c]isoquinolin-1-one [6(5H)-phenanthridinone] | 0.30 |
| 2-Nitro-6(5H)-phenanthridinone | 0.35 |
| 1,5-Dihydroxyisoquinoline | 0.39 |
| 2H-Benz[de]isoquinoline-1,3-dione (1,8-naphthalimide) | 1.4 |
| 2-Methyl-4(3H)-quinazolinone | 5.6 |
| 1-Hydroxyisoquinoline (isocarbostyril) | 7.0 |
| 2,4(1H,3H)-Quinazolinedione (benzoyleneurea) | 8.1 |
| Chlorthenoxazin | 8.5 |
| 4-Hydroxyquinazoline | 9.5 |
| 1(2H)-Phthalazinone | 12 |
| 2-Phenylchromone (flavone) | 22 |
| 3-Aminophthalhydrazide (luminol) | 23 |
| 2,3-Dihydro-1,4-phthalazinedione (Phthalhydrazide) | 30 |
| 5-Iodouridine | 43 |
| 2-Mercapto-4(3H)-quinazolinone | 44 |
| 2-Methyl-1,4-benzopyrone (2-methylchromone) | 45 |
| 5-Iodouracil | 71 |
| 3-Nitrophthalhydrazide | 72 |
| 4-Hydroxy-2-methylquinoline | 74 |
| 4-Hydroxyquinoline | 80 |
| Nicotinamide | 210 |

Preferred compounds of the invention include 3-aminobenzamide and 1, 5-dihydroxyisoquinoline.

To demonstrate the effectiveness of the present method for extending the proliferative capacity and lifespan of cells, human fibroblast cells lines (either W138 at Population Doubling (PDL) 23 or BJ cells at PDL 71) were thawed and plated on T75 flasks and allowed to grow in normal medium (DMEM/M199 plus 10% bovine calf serum) for about a week, at which time the cells were confluent, and the cultures were therefore ready to be subdivided. At the time of subdivision, the media was aspirated, and the cells were rinsed with phosphate buffered saline (PBS) and then trypsinized. The cells were counted with a Coulter counter and plated at a density of $10^5$ cells per cm$^2$ in 6-well tissue culture plates in DMEM/199 medium supplemented with 10% bovine calf serum and varying amounts (0, 10 μM, 100 μM, and 1 mM; from a 100X stock solution in DMEM/M199 medium) of a PADPRP inhibitor (3-aminobenzamide, purchased from Sigma). This process was repeated every ~7 days until the cells appeared to stop dividing.

Figure 2:
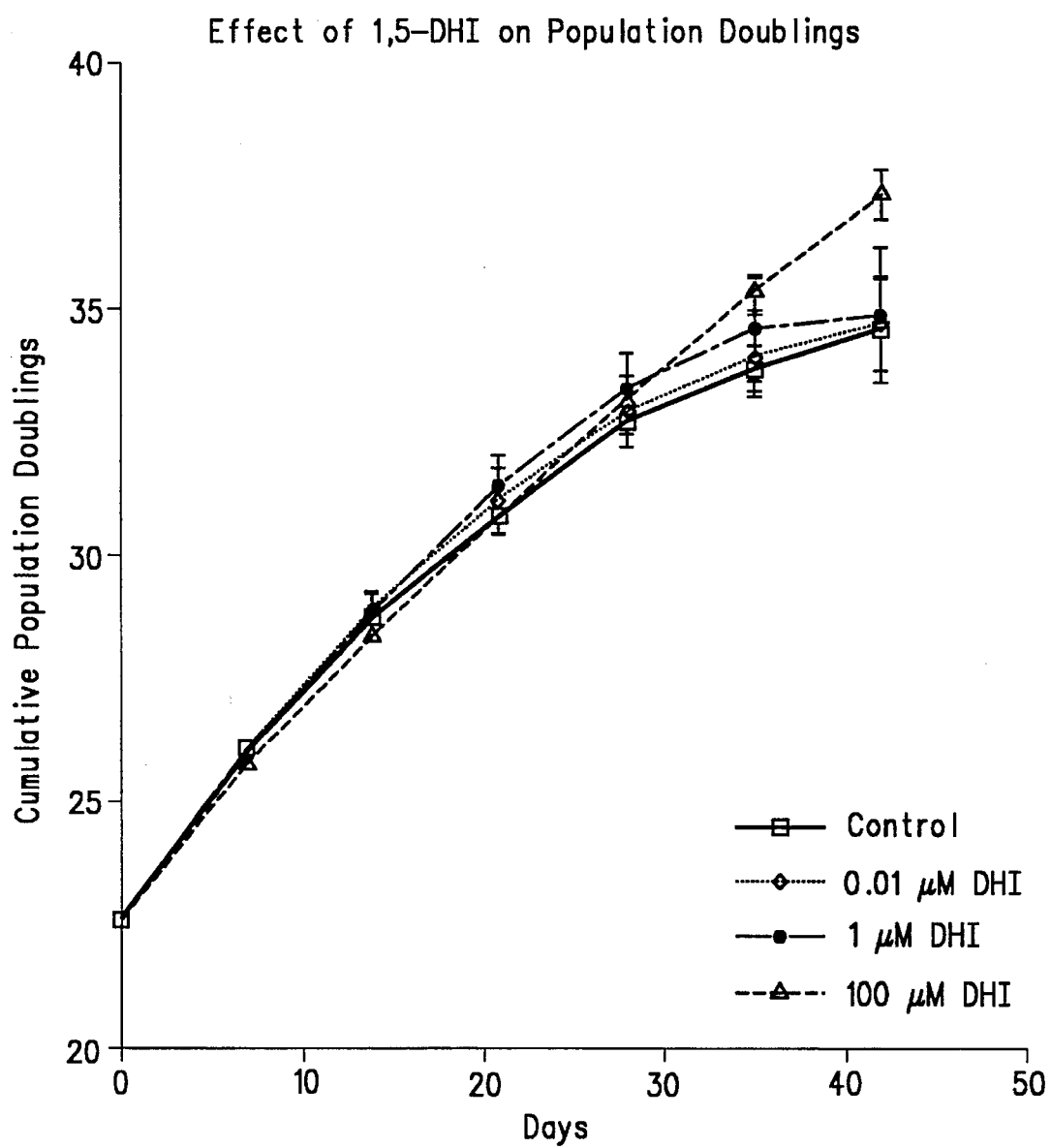
FIG. 2 shows the results of treating W138 cells with varying concentrations of 1, 5-dihydroxyisoquinoline (1, 5-DHI; also known as 1, 5-isoquinolinediol). The X-axis shows the number of days in culture, and the Y-axis shows the maximum achievable cumulative population doublings. At 100 μM (DMSO concentration 0.1%), the cells displayed an extension of their proliferative lifespan.

The results are shown in FIG. 1. As can be seen from the Figure, untreated (Control) cells reached senescence and stopped dividing after about 40 days in culture. While no effect was observed using 10 μM 3-AB, cells treated with 100 μM 3-AB did appear to have a longer lifespan than control cells, and cells treated with 1 mM 3-AB showed a dramatic increase in lifespan and proliferative capacity. The cells treated with 1 mM 3-AB were still dividing after 60 days in culture, a remarkable effect as compared with control cells. In a second example of the method, the results of which are shown in FIG. 2, the same procedure was conducted using the PADPRP inhibitor 1, 5-dihydroxyisoquinoline, and the results again show that the treated cells had increased proliferative capacity.

Thus, the method of the invention can be used to increase the lifespan of cells in vitro. While this aspect of the invention is important and of value for a wide variety of applications in cell culture methodology, a perhaps more important application of the present method involves the treatment of human and other disease. Because cell senescence is implicated in a wide variety of diseases, and may be proven to have a role in all diseases affecting the aged, the present invention offers remarkable promise in the treatment of disease.

In general, a suitable effective dose of a compound of the invention will be in the range of 0.001 to 100 milligram (mg) per kilogram (kg) of body weight of recipient per day, preferably in the range of 0.1 to 10 mg per kg of body weight per day. The desired dosage is preferably presented in one, two, three, four, or more subdoses administered at appropriate intervals throughout the day. These subdoses can be administered as unit dosage forms, for example, containing 5 to 10,000 mg, preferably 10 to 1000 mg of active ingredient per unit dosage form.

The composition used in these therapies can be in a variety of forms. These include, for example, solid, semisolid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., *Remington's Pharmaceutical Sciences,* Mack Publishing Co.: Easton, Penn., 17th Ed. (1985). Generally, administration will be by oral or parenteral (including subcutaneous, intramuscular, intravenous, and intradermal) routes. The therapeutic methods and agents of this invention can of course be used concomitantly or in combination with other methods and agents for treating a particular disease or disease condition.

While it is possible to administer the active ingredient of this invention alone, it is preferable to present it as part of a pharmaceutical formulation. The formulations of the present invention comprise at PADPRP inhibitor of this invention in a therapeutically or pharmaceutically effective dose together with one or more pharmaceutically or therapeutically acceptable carriers and optionally other therapeutic ingredients. Various considerations are described, e.g., in Gilman et al. (eds.) (1990) *Goodman and Gilman's: The Pharmacological Bases of Therapeutics,* 8th Ed., Pergamon Press; and *Remington's* supra, each of which is incorporated herein by reference. Methods for administration are discussed therein, e.g., for oral, intravenous, intraperitoneal, or intramuscular administration, and others.

The pharmaceutical compositions will be administered by topical, parenteral, or oral administration for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Topical administration typically involves the delivery of a Penn.DPRP inhibitor for percutaneous passage of the drug into the systemic circulation of the patient. The skin sites include anatomic regions for transdermally administering the drug as represented by the forearm, abdomen, chest, back, buttock, mastoidal area and the like. The PADPRP inhibitor is administered to the skin by placing on the skin a topical formulation comprising the PADPRP inhibitor or a transdermal drug delivery device that administers the drug, and which bandage is designed, shaped, sized, and adapted for easy placement and comfortable retention on the skin.

A variety of transdermal drug delivery devices can be employed with the compounds described herein. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509, 4,560,555, and 4,542,012.

In other embodiments, the PADPRP inhibitor will be delivered using a liquid reservoir system drug delivery device. These systems typically comprise a backing material, a membrane, an acrylate based adhesive, and a release liner. The membrane is sealed to the backing to form a reservoir. The drug and any vehicles, enhancers, stabilizers, gelling agents, and the like are then incorporated into the reservoir. See, e.g., U.S. Pat. Nos. 4,597,961, 4,485,097, 4,608,249, 4,505,891, 3,843,480, 3,948,254, 3,948,262, 3,053,255, and 3,993,073.

Matrix patches comprising a backing, a drug/penetration enhancer matrix, a membrane, and an adhesive can also be employed to deliver PADPRP inhibitors transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013, 4,460,562, 4,466,953, 4,482,534, and 4,533,540.

Also included within the invention are preparations for topical application to the skin comprising a PADPRP inhibitor, typically in concentrations in the range of from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. A preferred composition of the invention is a lotion containing a PADPRP inhibitor, such as arachidonic acid, linoleic acid, oleic acid, and/or nicotinamide, that is applied topically to treat skin aging. A more potent version of the lotion would include a PADPRP inhibitor such as 1, 5-DHI. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption.

For delivery to the buccal or sublingual membranes, typically an oral formulation, such as a lozenge, tablet, or capsule will be used. The method of manufacture of these formulations is known in the art, including but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example, as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly or intravenously. Thus, this invention provides compositions for intravenous administration which comprise a solution of the PADPRP inhibitor dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol or the like. These compositions will sometimes be sterilized by conventional, well known, sterilization techniques, or can be sterile filtered. The resulting solutions can be packaged for use as is, or lyophilized, the lyophilized preparation being combined with a sterile solution prior to administration. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference.

Liquid pharmaceutically administerable compositions can, for example, be prepared by dissolving, dispersing, etc., an active compound as defined above and optional pharmaceutical adjuvants in a excipient, such as, for example, water, saline, aqueous dextrose, glycerol, ethanol, olive oil and other lipophilic solvents, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's*, supra. The composition or formulation to be administered will, in any event, contain an effective amount of the active compound.

For solid compositions, conventional nontoxic solid carriers can be used, which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

With regard to the prophylactic applications of the present invention, the present invention provides useful methods to delay the progression of AIDS. While not wishing to be bound by theory, the present inventor believes that immune cell senescence may induce HIV 2O expression, which is known to be increased upon DNA damage (see, e.g., Valerie et al., 1988, *Nature* 333:78–81, and Stein et al., 1989, *Mol. Cell. Biol.* 5169–5181). One can therefore administer a PADPRP inhibitor according to the method of the invention to those infected with HIV to delay the onset of AIDS.

One can also employ a novel screening method of the invention to find more effective inhibitors of PADPRP and to find any compound that delays the onset of senescence and/or delays expression of HIV in HIV-infected cells. In this method, one first constructs a recombinant vector that comprises the HIV long terminal repeat (LTR) promoter positioned to drive expression of a reporter gene product (a reporter gene is a gene that produces a gene product that can be readily assayed, i.e., the betagalactosidase gene, the alkaline phosphatase gene, etc.). This vector is used to transform suitable cell lines, such as eukaryotic fibroblast or lymphocyte cell lines, which when grown to senescence should show induction of expression of the reporter gene. In the screen, one assays whether test compounds delay, inhibit, or prevent the induction of expression of the reporter gene caused by senescence. Compounds that could delay senescence would delay, inhibit, or prevent the induction of expression of the reporter gene and would be useful for purposes of the present invention not only generally to prevent cell senescence but also specifically to treat AIDS.

The foregoing text describes various aspects of the invention and how the invention can be practiced. The description of the invention is not intended to provide an exhaustive description of the many different embodiments of the invention. All publications and patent applications cited above are hereby incorporated herein by reference as if each individual publication or patent application were specifically and individually indicated to be incorporated by reference. Thus, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for delaying the onset of cell senescence associated with skin aging in a human comprising administering to fibroblast cells in the human an amount of an isoquinoline PADPRP inhibitor effective to increase the maximum achievable number of cumulative population doublings of the fibroblast cells, whereby the proliferative capacity of the fibroblast cells is increased.

2. The method of claim 1 wherein said inhibitor is selected from the group of inhibitors consisting of 2H-benz isoquinolin-1-one; 1,5-dihydroxyisoquinoline; 2H-benzisoguinoline-1,3-dione; and 1-hydroxyisoquinoline.

3. The method of claim 1 wherein the inhibitor is applied transdermally.

* * * * *